United States Patent [19]

Hakamatsuka

[11] Patent Number: 4,950,294

[45] Date of Patent: Aug. 21, 1990

[54] COMPOSITE STRUCTURE USEFUL AS ARTIFICIAL BONES

[75] Inventor: Yasuharu Hakamatsuka, Hachioji, Japan

[73] Assignee: Olympus Optical Co., Ltd., Tokyo, Japan

[21] Appl. No.: 188,697

[22] Filed: May 2, 1988

Related U.S. Application Data

[63] Continuation of Ser. No. 834,811, Feb. 28, 1986, abandoned.

[30] Foreign Application Priority Data

Mar. 6, 1985 [JP] Japan .................................. 60-43927

[51] Int. Cl.$^5$ .............................................. A61F 2/28
[52] U.S. Cl. ................................... 623/16; 433/201.1;
427/2; 428/702; 501/105; 501/152
[58] Field of Search ................. 623/16; 428/702, 433;
501/105, 152; 106/35; 427/2

[56] References Cited

U.S. PATENT DOCUMENTS

| | | | |
|---|---|---|---|
| 4,155,124 | 5/1979 | Kawahara et al. | 623/16 |
| 4,168,326 | 9/1979 | Broemer et al. | 623/16 X |
| 4,171,544 | 10/1979 | Hench et al. | 623/16 |
| 4,259,072 | 3/1981 | Hirabayashi et al. | 623/16 X |
| 4,366,183 | 12/1982 | Ghommidh et al. | 623/16 X |
| 4,524,100 | 6/1985 | Shimuzu et al. | 428/283 |
| 4,587,225 | 5/1986 | Tsukuma et al. | 501/152 X |
| 4,595,663 | 6/1986 | Krohn et al. | 501/152 X |
| 4,599,085 | 7/1986 | Riess et al. | 623/16 |

FOREIGN PATENT DOCUMENTS 59-112908  6/1984  Japan .

OTHER PUBLICATIONS

Journal of the American Ceramic Society, Sep.-Oct. vol. 60, pp. 428-435 (1977).

Primary Examiner—Alan W. Cannon
Attorney, Agent, or Firm—Frishauf, Holtz, Goodman & Woodward

[57] ABSTRACT

A composite structure useful as an implant material in bones includes a matrix made of $Al_2O_3$—$ZrO_2$ ($Y_2O_3$) ceramic material. The surface of the matrix is non-monocrystallized. A bio-active layer covers the matrix surface.

30 Claims, 1 Drawing Sheet

COMPOSITE STRUCTURE USEFUL AS ARTIFICIAL BONES

This application is a continuation, of application Ser. No. 834,811, filed Feb. 28, 1986, now abandoned.

BACKGROUND OF THE INVENTION

1. Field of the Invention

The present invention relates to a composite structure useful as an artificial implant material such as artificial dental roots, artifical bones and the like.

2. Description of the Prior art

Materials for artificial bones must have good affinity with vital tissues, must easily, chemically bond to natural bones and must have good mechanical properties.

A sintered apatite body is known as material for aritificial bones. It is made in the following way. First, calcium carbonate powder is heated. An aqueous solution of phosphoric acid is then added to the heated powder, thus preparing apatite powder. The apatite powder is press-formed and sintered, providing the sintered body. The body has good affinity with vital tissues and excellent chemical bondability with natural bones. Its mechanical properties can be improved to some extent by special treatments. The body, however, does not have a sufficient mechanical strength.

Alumina (sapphire) is also used as material for artificial bones. It has a good affinity with vital tissues and a great mechanical strength, but cannot chemically bond to natural bones. To compensate for the bondability of alumina, holes or concaves are cut in an alumina body, and some portions of a natural bone are forcibly fitted in these holes or concaves, whereby the bones is fastened to the alumina body. However, the joint between the bone and the alumina body tends to loosen when the bone shrinks or deforms with lapse of time.

$Na_2O$—$CaO$—$SiO_2$—$P_2O_5$ system glass and $Na_2O$—$K_2O$—$MgO$—$CaO$—$SiO_2$—$P_2O_5$ ($CaF_2$) system glass ceramics have good affinity with vital tissues and can chemically bond to natural bones. Their mechanical properties are, however, poor.

Various ceramic materials exhibiting good affinity with vital tissues, excellent bondability to natural bones and sufficient mechanical strength are now being researched. The data presented in the 15th Lecture on Ceramics (Bio-ceramics), 1984discloses that zirconia has good affinity with vital tissues. Also, Japanese Patent Disclosure No. 59-112908 discloses some materials for artificial bones.

SUMMARY OF THE INVENTION

An object of the present invention is to provide an implant material having good affinity with vital tissues, chemical bondability to natural bones and a great mechanical strength..

The invention provides a composite structure useful as an implant material, comprisig a matrix formed of $Al_2O_3$—$ZrO_2$ ($Y_2O_3$) ceramic material and having a non-monocrystallized surface layer, and a bio-active layer covering at least the non-monocrystallized surface layer.

BRIEF DESCRIPTION OF THE PREFERRED EMBODIMENTS

Figure 1:
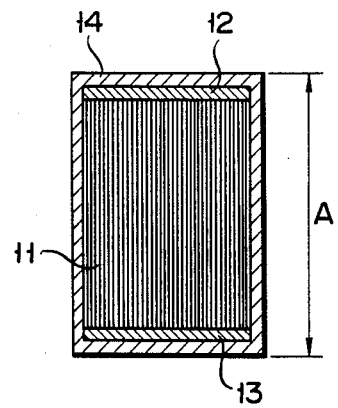
FIGS. 1 to 4 illustrate the composite structures according to the present invention.

The present invention will be explained in detail with reference to the drawings attached hereto. The same parts are indicated with the same numerals in these drawings.

The composite structure of this invention, useful as material for artificial bones, has a matrix of $Al_2O_3$—$ZrO_2$ ($Y_2O_3$) ceramic material. The ceramic material is generally composed of 10 to 40 mol % of alumina, 58 to 88 mol % of zirconia, and 0.5 to 2 mol % of yttria.

The matrix can be provided as an orientated crystal prepared by melting an $Al_2O_3$—$ZrO_2$ ($Y_2O_3$) ceramic material of an eutectic composition (i.e., alumina 20 mol %, zirconia 78 mol % and yttria 2 mol %) at 2800° C. to 3000° C., and then cooling and solidifying the molten material. The solidification is conducted in one direction (directional solidification), preferably by cooling the molten material at rate of 1° to 10° C./min, while maintaining a vertical temperature gradient of 50° to 100° C. or more. J. Am. Ceramic Soc., Sept. - Oct., 60, 428–435 (1977) is incorporated herein by reference for disclosing directional solidification of eutectics which may be applied in making the orientated crystal used in the present invention.

Alternatively, the matrix can be provided in the form of a sintered body by adding an organic binder to powder of the ceramic material, press-forming the resultant mixture, and sintering the formed body under a pressure of 10 to 50 kg/cm2 at a temperature of 1500° to 2000° C.

The matrix, whether the orientated crystal or the sintered body, is often chemically denatured over years. Consequently, the mechanical strength of the matrix, particularly compression strength and abrasion strength, decreases. In particular, the matrix made of the orientated crystal is weak to the stress applied along the orientation axis, though considerably strong to the stress acting in the direction normal to the crystal orientation; it becomes weaker to the axial stress as time lapses.

In the present invention, at least the surface layer of the matrix, or, preferably, the entire matrix surface, is non-monocrystallized (or rendered amorphous or polycrystalline). This surface layer includes at least the portion which will be connected to a natural bone. When the matrix is the orientated crystal, this specific portion of the surface layer is generally an end located in a plane perpendicular to the orientation axis.

The non-monocrystallization is accomplished by applying a laser beam to the surface layer by, for example, a carbon dioxide gas laser, thereby fusing this layer, and then cooling the layer at room temperature. Usually the non-monocrystallized layer has a thickness of 0.1 to 10 μm.

The matrix is covered with a bio-active layer, thus making the matrix bio-active. The word "bio-active" refers to substances that have affinity with vital tissues (biocompatibility) and good chemical bondability with natural bones. It is desired that the bio-active layer be formed of phosphate salt material containing a relatively large amount of calcium or Hench glass of $SiO_2$—$CaO$—$B_2O_3$—$Na_2O$—$P_2O_5$ system. Tricalcium phosphate, $Ca_3(PO_4)_2$, and hydroxy apatite, $Ca_5(PO_4)_3OH$, are desired phosphates. The thickness of the bio-active layer is generally 2 to 3 μm.

A apatite layer or a β-TCP layer, either being a bio-active layer, cay be formed in the following wet process. First, a water-soluble calcium salt (e.g., calcium nitrate), a calcium complexing agent (ethylenediaminetetraacetic acid) and a water-soluble phosphate (diammonium hydrogen phosphate) are mixed in a molar ratio of 1:1—1.2:0.6. Water is added to the resultant mixture, thereby preparing an aqueous solution having pH of 6 to 11. An aqueous solution of hydrogen peroxide is added to the aqueous solution in such an amount that its content is 2–7% by weight, thereby providing a solution of calcium phosphate. This solution is heated to 80° C., and the matrix of $ZrO_2$—$Al_2O_3$ ($Y_2O_3$) is immersed in the hot solution. As a result, calcium phosphate (hydroxy apatite or tricalcium phoshate) precipitates on the surface of the matrix. The matrix is heat-treated at 800° to 1200° C., whereby the calcium phosphate layer is firmly bonded to the matrix.

FIG. 1 shows the composite structure of the present invention, having matrix 11 of an oriented crystal. Ends 12 and 13 of matrix 11, which extend at right angles to the orientation axis A, are formed of amorphous or polycrystalline $Al_2O_3$—$ZrO_2$ ($Y_2O_3$) ceramic material. The entire surfaces of matrix is covered with bio-active layer 14.

Figure 2:
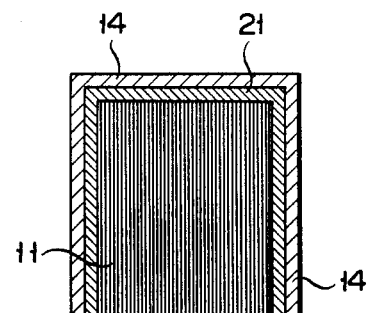

FIG. 2 illustrates another composite structure according to the invention. This is identical with the material of FIG. 1, except that non-monocrystallized layer 21 covers all surfaces of a matrix 11.

When the matrix is formed of the sintered body, the corresponding composite structure has a structure the same as in FIG. 1 or 2, except that the matrix is formed of the sintered body.

Figure 3:
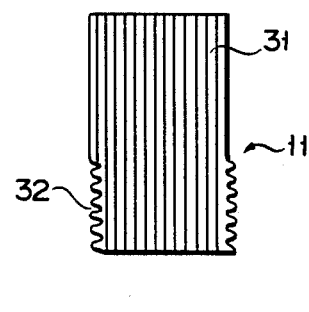
Figure 4:
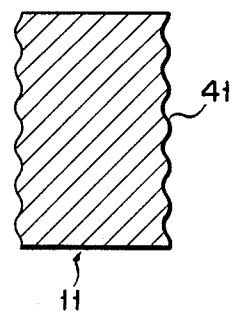

FIGS. 3 and 4 show still other composite materials whose sides are not flat, unlike the materials of FIGS. 1 and 2. More specifically, the structure of FIG. 3 has grooves 31 cut in the sides and projections 32 protruding from portions of the sides, and the structure of FIG. 4 has projections 41 protruding from the entire sides.

EXAMPLE 1

An orientated crystal was obtained by melting an $Al_2O_3$—$ZrO_2$ ($Y_2O_3$) ceramic material having the eutectic composition and by cooling the molten material in one direction at a rate of 2° C./min, thereby solidifying the molten material while maintaining a vertical temperature gradient of 100° C. The crystal was cut into five prisms, each measuring 5×5 ×20 mm. They were ground on all surfaces. The prisms were than subjected to the three-point loading test, thereby measuring their bending strengths. The load was applied on them in the direction normal to their orientation axis. The results were as shown in the following table, which includes the bending strengths of single crystal sapphire (load applied along C axis) and the human bone, i.e., the data given in *Clinical Orthopaedics and Related Research*, 73, 210 (1970).

| Sample | Average Bending Strength (kg/cm$^2$) | Standard Deviation (kg/cm$^2$) |
| --- | --- | --- |
| This Invention | 15,000 | 250 |
| Sapphire | 8,000 | 200 |
| Human bone | 300–1,900 | |

As the above table indicates, the orientated crystal of the present invention is mechanically stronger than sapphire, or strong enough to be used as the material for artificial bones.

EXAMPLE 2

An orientated crystal obtained as in Example 1 was cut into several columns. A carbon gas laser beam was applied to the columns on all surface, thus fusing the surface layer of each column. The columns were then left to stand. Thereafter, β-TCP (tricalcium phosphate) was formed by the wet process on the entire surface of each column, thus providing a sample, 2 mm thick and 5 mm long. Several rabbits were incised at the scalp. A groove, about 2 mm wide and about 2 mm deep, was cut in the cranial bone with a fissure bur attached to the dentist's electric engine. The samples were inserted in the grooves, and the scalps were sutured. The portion of the cranial bone having the sample was cut out of a first rabbit, three weeks later. That portion of the bone having the sample was cut out of a second rabbit, six weeks later. That portion of the bone having the sample was cut from a third rabbit, nine weeks later. These bones were fixed with a 2.5% glutaraldehyde solution, dehydrated with alcohol, dried at critical point, and examined under a scanning electron microscope.

In the case of the sample inserted in the bone for three weeks, hydroxy apatite and collagen fiber network attached thereto were found on the surface. As for the sample inserted in the bone for six weeks, a collagen fiber network and platelike structure consisting of collagen fiber and the vital apatite had been formed. The sample inserted in the bone for nine weeks was fixed and immovable due to the regeneration of the cranical bone.

As mentioned above, the composite structure of the invention is useful as an artificial implant material in bones, such as artificial dental roots, artificial bones and the like, and has better properties than the conventional artificial implant materials. Its properties change but very slightly with lapse of time. It can chemically bond to natural bones and does not loosen.

What is claimed is:

1. A composite structure useful as an implant material in bone, comprising:
   a matrix made of $Al_2O_3$—$ZrO_2$—$Y_2O_3$ ceramic material having a composition of 10 to 40 mol % of $Al_2O_3$, 88 to 58 mol % of $ZrO_2$ and 0.5 to 2 mol % of $Y_2O_3$;
   an amorphous surface layer; and
   a bio-active layer covering at least said amorphous layer.

2. The composite structure according to claim 1, wherein said matrix comprises an orientated crystal of said ceramic material.

3. The composite structure according to claim 1, wherein said ceramic material has eutectic composition.

4. The composite structure according to claim 1, wherein said matrix comprises a sintered body of said ceramic material.

5. The composite structure according to claim 1, wherein said surface layer has a thickness of 0.1 to 10 μm.

6. The composite structure according to claim 1, wherein said bio-active layer is made of at least one material selected from the group consisting of Hench glass, tricalcium phosphate and hydroxyapatite.

7. The composite structure according to claim 6, wherein said bio-active layer has a thickness of 2 to 3 μm.

8. The composite structure according to claim 1, wherein said amorphous surface layer covers all surface of said matrix.

9. The composite structure according to claim 1, wherein said bio-active layer covers all surface of said amorphous surface layer.

10. The composite structure according to claim 1, wherein said matrix has at least one side, said at least one side having grooves and projections thereon.

11. The composite structure according to claim 10, wherein said matrix has two opposing sides, each of said sides having grooves and projections thereon.

12. The composite structure according to claim 1, wherein said matrix has at least one side, and has a plurality of spaced apart projections protruding therefrom along the entire length of said at least one side.

13. The composite structure according to claim 12, wherein said matrix has two opposing sides, and has said spaced apart projections protruding from said two opposing sides along the entire length of said two opposing sides.

14. The composite structure according to claim 1 wherein said bio-active layer is made of at least one material selected from the group consisting of tricalcium phosphate and hydroxy apatite.

15. The composite structure according to claim 10 wherein said bio-active layer has a thickness of 2 to 3 microns.

16. The composite structure according to claim 1, wherein a surface layer of said matrix has been irradiated with laser beam to provide said amorphous surface layer.

17. A composite structure useful as an implant material in bone, comprising:
a matrix made of $Al_2O_3$—$ZrO_2$—$Y_2O_3$ ceramic material having a composition of 10 to 40 mol % of $Al_2O_3$, 88 to 58 mol % of $ZrO_2$ and 0.5 to 2 mol % of $Y_2O_3$, a surface layer of said matrix having been amorphitized by irradiation with a laser beam; and
a bio-active layer covering at least said amorphitized layer of the matrix.

18. The composite structure according to claim 17, wherein said laser beam in a carbon dioxide gas laser.

19. The composite structure according to claim 17, wherein said matrix comprises an oriented crystal of said ceramic material.

20. The composite structure according to claim 17, wherein said ceramic material has a eutectic composition.

21. The composite structure according to claim 17, wherein said matrix comprises a sintered body of said ceramic material.

22. The composite structure according to claim 17, wherein said surface layer has a thickness of 0.1 to 10 $\mu$m.

23. The composite structure according to claim 17, wherein said bio-active layer is made of at least one material selected from the group consisting of Hench glass, tricalcium phosphate and hydroxyapatite.

24. The composite structure according to claim 23, wherein said bio-active layer has a thickness of 2 to 3 $\mu$m.

25. The composite structure according to claim 17, wherein said amorphous surface layer covers the whole surface of said matrix.

26. The composite structure according to claim 17, wherein said bio-active layer covers the whole surface of said amorphous surface layer.

27. The composite structure according to claim 17, wherein said matrix has at least one side, said at least one side having grooves and projections thereon.

28. The composite structure according to claim 27, wherein said matrix has two opposing sides, each of said sides having grooves and projections thereon.

29. The composite structure according to claim 27, wherein said bio-active layer has a thickness of 2 to 3 microns.

30. The composite structure according to claim 17, wherein said bio-active layer is made of at least one material selected from the group consisting of tricalcium phosphate and hydroxy apatite.

* * * * *